(12) United States Patent
Witschey et al.

(10) Patent No.: US 8,526,695 B2
(45) Date of Patent: Sep. 3, 2013

(54) MAGNETIC RESONANCE IMAGING FOR DIAGNOSTIC MAPPING OF TISSUES

(75) Inventors: Walter R. Witschey, Philadelphia, PA (US); Ari Borthakur, Philadelphia, PA (US); Ravinder Reddy, Gladwyne, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 999 days.

(21) Appl. No.: 12/595,462

(22) Filed: Oct. 9, 2009

(65) Prior Publication Data

US 2010/0166278 A1 Jul. 1, 2010

Related U.S. Application Data

(63) Continuation of application No. PCT/US2008/004780, filed on Apr. 11, 2008.

(60) Provisional application No. 60/923,215, filed on Apr. 11, 2007.

(51) Int. Cl.
*G06K 9/00* (2006.01)
*G06K 9/36* (2006.01)
*G06K 9/32* (2006.01)

(52) U.S. Cl.
USPC ........... 382/131; 382/129; 382/130; 382/132; 382/284; 382/294

(58) Field of Classification Search
USPC .................. 382/128–132, 284, 294
See application file for complete search history.

(56) References Cited

U.S. PATENT DOCUMENTS

| 5,303,705 | A  | * | 4/1994  | Nenov .......................... 600/410 |
| 6,681,132 | B1 |   | 1/2004  | Katz |
| 6,836,114 | B2 | * | 12/2004 | Reddy et al. ................... 324/307 |
| 6,943,033 | B2 | * | 9/2005  | Van Zijl et al. ............... 436/173 |
| 2003/0170745 | A1 |  | 9/2003 | Pereira |

FOREIGN PATENT DOCUMENTS

WO  PCT/US2008/004780    4/2008

OTHER PUBLICATIONS

Sprawls, Perry, "Magnetic Resonance Imaging: Principles, Methods, and Techniques" Medical Physics Publishing 2000.*
Liao et al., "A New Framework of Quantifying Differences Between Images by Matching Gradient Fields and Its Application to Image Blending" IEEE 2003.*
Witschey et al, "Compensation for Spin-Lock Artifacts Using an Off-Resonance Rotary Echo in T1poff-Weighted Imaging" Magn Reson Med., Jan. 2007.*
Bibliography, multiple authors "Current awareness in NMR in biomedicine" NMR Biomed 2007 20:624-631.*

(Continued)

*Primary Examiner* — Neal Sereboff
(74) *Attorney, Agent, or Firm* — Woodcock Washburn, LLP

(57) ABSTRACT

Methods of, and systems for, magnetic resonance imaging of diagnostic mapping of tissues, where sodium mapping is performed individually, as well as in combination with other images of tissue, such as T1ρ, T2, and/or T1-weighted images. In one method embodiment, a sodium image of the tissue is acquired during the same scanning session. Maps are constructed of each of the first and sodium images individually, and in combination, and further facilitate viewing in combination with each other as a single, blended image of the tissue. Maps of the images may be displayed individually or in combination with each other.

20 Claims, 4 Drawing Sheets

(56) References Cited

OTHER PUBLICATIONS

Borthakur et al., "Sodium and T1ρ MRI for molecular and diagnositic imaging of articular cartilage" NMR in Biomedicine 2006; 19:781-821.*
McReynolds, Tom "Programming with OpenGL: Advanced Rendering" SIGGRAPH '96 Course, Sep. 29, 1999.*
Akella, "Proteoglycan-Induced Changes in T1Rho-Relaxation of Articular Cartilage at 4T," Magn. Reson. Med. 46:419-423 (2001).
Aronen, "3D Spin-Lock Imaging of Human Gliomas," Magn. Reson. Imag. 17:1001-1010 (1999).
Bashir, "Gd-DTPA2—as a Measure of Cartilage Degradation," Magn. Reson. Med. 36:665-673 (1996).
Borthakur, "Three-Dimensional T1Rho-Weighted MRI at 1.5 Testa," J Magn Reson Imaging 17(6):730-736 (2003).
Burstein, "Protocol Issues for Delayed Gd(DTPA)2—Enhanced MRI (dGEMRIC) for Clinical Evaluation of Articular Cartilage," Magn. Reson. Med. 45:36-41 (2001).
Dardzinski, "Spatial Variation of T2 in Human Articular Cartilage," Radiology 205(2):546-550 (1997).
Duvvuri, "T1Rho-Relaxation in Articular Cartilage: Effects of Enzymatic Degredation," Magn.Reson.Med. 38:863-867 (1997).
Duvvuri, "Human Knee: In Vivo T1Rho-Weighted MR Imaging at 1.5T—Preliminary Experience," Radiology 220:822-826 (2001).
Felson, "Epidemiology of Hip and Knee Osteoarthritis," Epidemiol. Prev. 10:1-28 (1988).
Felson, "The Incidence and Natural History Knee Osteoarthritis in the Elderly," Arthritis Rheum. 38:1500-1505 (1995).
Grushko, "Some Biochemical and Biophysical Parameters for the Study of the Pathogenesis of Osteoarthritis: A Comparison Between the Processes of Ageing and Degeneration in Human Hip Cartilage," Conn. Tiss. Res. 19:149-176 (1989).
Guccione, "The Effects of Specific Medical Conditions on the Functional Limitations of Elders in the Framingham Study," Am. J. Public Health 84:351-358 (1994).
Lohmander, "Articular cartilage and osteoarthrosis. The role of molecular markers to monitor breakdown, repair and disease*," J. Anatomy 184:477-492 (1994).
Mankin, "Biochemical and Metabolic Abnormalities in Articular Cartilage from Osteo-Arthritic Human Hips," J. Bone Joint Surg-Am. 53:523-537 (1971).
Markkola, "Spin Lock and Magnetization Transfer Imaging of Head and Neck Tumors," Radiology 200:369-375 (1996).
Mlynarik, "The Role of Relaxation Times in Monitoring Proteoglycan Depletion in Articular Cartilage," J. Magn. Reson. Imaging 10:497-502 (1999).
Mosher, "Change in Knee Cartilage T2 at MR Imaging after Running: A Feasibility Study1," Radiology 234 (1):245-249 (2005).
Peterfy, "Recent Advantages in Magnetic Resonance Imaging of the Musculoskeletal System," Radiol. Clin. North Am. 32:291-311 (1994).
Peterfy, "Emerging Applications of Magnetic Resonance Imaging in the Evaluation of Articular Cartilage," Radiol. Clin. North Am. 34:195-213 (1996).
Peterfy, "Scratching the surface: articular cartilage disorders in the knee," Magn. Reson, Imaging Clin. N. Amer. 8:409-430 (2000) (Abstract Only).
Recht, "MR Imaging of Articular Cartilage: Current Status and Future Directions," Am. J. Roent. 163:283-290 (1994).
Reddy, "Sodium MRI of Human Articular Cartilage In Vivo," Magn. Reson. Med. 39:697-701 (1998).
Redfield, "Nuclear Magnetic Resonance Saturation and Rotary Saturation in Solids," Phys. Rev. 98:1787 (1955).
Rizi, "Proton T1Rho-Dispersion Imaging of Rodent Brain at 1.9T," J. Magn. Reson. Imaging 8:1090-1096 (1998).
Santyr, "Spin Locking for Magnetic Resonance Imaging with Application to Human Breast," Magn. Reson. Med. 12:25-37 (1989).
Sepponen, "A Method for T1Rho Imaging," J. Computer Assisted Tomography 9:1007-1011 (1985).
Shapiro, "Sodium Visibility and Quantitation in Intact Bovine Articular Cartilage Using High Field 23Na MRI and MRS," J. Magn. Reson. 142:24-31 (2000).
Shapiro, "23Na MRI Accurately Measures Fixed Charge Density in Articular Cartilage," Magn. Reson. Med. 47:284-291 (2002).
Sofka, "Magnetic Resonance Imaging of the Wrist," Radiology 5:217-226 (2001).
Wheaton, "Pulse Sequence for Multislice T1RHO-Weighted MRI," Magn. Reson. Med. 51(2):362-369 (2004).
Yelin, "The Economics of Osteoarthritis," In: Brandt K, Doherty M, Lohmander LS, editors. Osteoarthritis. Oxford: Oxford Medical Publ.; 1998. 23-30.

* cited by examiner

MAGNETIC RESONANCE IMAGING FOR DIAGNOSTIC MAPPING OF TISSUES

CROSS-REFERENCE TO RELATED APPLICATIONS

The present patent application is a continuation of International Application PCT/US2008/004780, filed Apr. 11, 2008 and published Oct. 23, 2008, which claims benefit of U.S. Provisional Application Ser. No. 60/923,215, filed Apr. 11, 2007, each of which is incorporated herein by reference.

STATEMENT OF GOVERNMENT INTEREST

This invention was made with government support by Grants R01AR045404 and R01AR051041 awarded by The National Institutes of Health, and performed at a NIH supported resource center (NIH RR02305). The government has certain rights in this invention.

FIELD OF THE INVENTION

The present invention relates to magnetic resonance imaging (MRI), and more particularly, a magnetic resonance (MR) method and system for diagnostic mapping of tissues.

BACKGROUND OF THE INVENTION

Osteoarthritis (OA) affects more than half of the population above the age of 65 (Felson, *Epidemiol. Prev.* 10:1-28 (1988); Felson, *Arthritis Rheum.* 38:1500-1505 (1995)) and has a significant negative impact on the quality of life of elderly individuals (Guccione et al., *Am. J. Public Health* 84:351-358 (1994)). The economic costs in the US from OA have been estimated to be more than 1% of the gross domestic product. OA is now increasingly viewed as a metabolically active joint disorder of diverse etiologies.

Articular cartilage is a connective tissue consisting of relatively few cells and a highly charged and hydrated extracellular matrix (ECM). The constituents of the ECM are proteoglycans (PG), collagen, and non-collagenous proteins and water (Grushko et al., *Conn. Tiss. Res.* 19:149-176 (1989); Lohmander, *J. Anatomy* 184:477-492 (1994); Mankin et al., *J. Bone Joint Surg-Am.* 53:523-537 (1971)). Despite its remarkable durability, degeneration of articular cartilage can result from either noninflammatory processes, such as osteoarthritis (OA), or inflammatory processes, such as rheumatoid arthritis (RA). The biochemistry of early stage OA is associated with loss of PG concentration, possible changes in the size of collagen fibril and aggregation of PG, increased water content, and increased rate of synthesis and degradation of matrix macromolecules (Grushko et al., 1989; Lohmander, 1994). All of these changes in the macromolecular matrix lead to an alteration in the mechanical properties of cartilage with the result that it can no longer serve as an effective load-bearing material.

As the disease progresses to its late stages, joint surface replacement (arthroplasty) is the only effective treatment. More recently, there have been efforts in developing novel techniques for the treatment of OA, such as chondro-protective drugs and re-population of the cartilage defects by chondrocyte precursor cells with subsequent regeneration of the cartilage. Nevertheless, while current therapies have largely been directed toward symptomatic relief of the disease, i.e., the development of drugs in animals that have shown the potential of protecting the macromolecules in cartilage from breakdown, they have proven to date to be ineffective for halting the progression of OA. Moreover, a direct and accurate, yet noninvasive, technique for validating the efficacy of these drugs in vivo, involving chondroprotective therapies, cartilage grafting, gene therapy and tissue engineering over the long duration of the OA disease (10-20 years) in humans, and to assess their effect on molecular changes associated with early stages of cartilage degeneration that always precede structural changes.

Computed tomography (CT) and magnetic resonance imaging (MRI). Unfortunately, arthrography is an invasive technique that causes pain and discomfort to the subjects, and is, therefore, not ideal for routine clinical use. CT cannot provide biochemical information, but conventional MRI can assess cartilage lesions and provide morphologic information about the cartilage damage. Thus, MRI has become the modality of choice for imaging joints due to its excellent definition of ligaments, cartilage, bone, muscle, fat and superior soft tissue contrast (Smith, *Magn. Reson. Imaging Clin. N. Am.* 3:229-248 (1995); Sofka et al., *Radiology* 5:217-226 (2001)). For two decades, proton magnetic resonance imaging (MRI) has shown its efficacy in the noninvasive analysis of soft tissues, particularly in the diagnosis of tendinomuscular and osteoarticular diseases (Peterfy et al., *Radiol. Clin. North Am.* 34:195 (1996); Peterfy, *Magn. Reson, Imaging Clin. N. Amer.* 8:409-430 (2000)). Nevertheless, while conventional MRI can be used to quantify structural changes in articular cartilage, it cannot quantify early-stage molecular changes. Thus, the current lack of adequate methods for quantifying these changes has hampered research directed towards the development of potential disease modifying agents.

Joint space narrowing determined from conventional radiographs is widely accepted as an indication for early diagnosis of OA. However, it does not yield accurate and quantifiable results on molecular changes that precede morphological changes.

Conventional proton MR techniques have been shown to provide information about late stages of degeneration in which structural defects are present (Recht et al., *Am. J. Roent.* 163:283-290 (1994); Peterfy et al., *Radiol. Clin. North Am.* 32:291-311 (1994)). Recently, delayed gadolinium (Gd)-enhanced proton MRI of cartilage (dGEMRIC) (Bashi et al., *Magn. Reson. Med.* 36:665-673 (1996); Burstein et al., *Magn. Reson. Med.* 45:36-41 (2001); Mlynarik et al., *J. Magn. Reson. Imaging* 10:497-502 (1999)), positively charged nitroxide based techniques (Lattanzio et al., *Trans. Orthop. Res. Soc.* 25:1024 (2000)), and sodium MRI (Reddy et al., *Magn. Reson. Med.* 39:697-701 (1998); Shapiro et al., *J. Magn. Reson.* 142:24-31 (2000); Shapiro et al., *Magn. Reson. Med.* 47:284-291 (2002)) have been employed to measure PG changes in cartilage both in vivo and in vitro. However, these techniques have some practical limitations. In dGEMRIC, long waiting period between contrast agent injection and imaging and variation in intra tissue Gd-relaxivity may contribute to the errors in PG quantization, thereby reducing the accuracy of this technique in the detection of OA. Although sodium MR imaging has high specificity towards proteoglycans, it has an inherently low sensitivity and requires special radio-frequency hardware modifications before it can be used with a routine clinical imaging unit.

Spin lattice relaxation time in the rotating frame (T1$\rho$) has been shown to be sensitive to changes in PG content of cartilage (Duvvuri et al., *Magn. Reson. Med.* 38:863-867 (1997); Akella et al., *Magn. Reson. Med.* 46:419-423 (2001)). It is well suited for probing macromolecular slow motions at high static fields without modifying MR system hardware (Sepponen et al., *J. Computer Assisted Tomography* 9:1007-1011

(1985); Santyr et al., *Magn. Reson. Med.* 12:25-37 (1989)) and provides an alternative contrast compared to conventional MRI methods.

Since the first description by Redfield (*Phys. Rev.* 98:1787 (1955)), spin-locking techniques have been used extensively, to investigate the low frequency interactions between the macromolecules and bulk water. Several authors have investigated the T1ρ dispersion characteristics of biological tissues, including brain (Aronen et al., *Magn. Reson. Imag.* 17:1001-1010 (1999); Rizi et al., *J. Magn. Reson. Imaging* 8:1090-1096 (1998)), tumors (Aronen et al., *Magn. Reson. Imag.* 17:1001-1010 (1999); Markkola et al., *Radiology* 200:369-375 (1996)), and articular cartilage (Mlynarik et al., 1999; Akella et al., 2001; Duvvuri et al., 1997; Duvvuri et al., *Radiology* 220:822-826 (2001)). These studies have demonstrated the potential value of T1ρ-weighting in evaluating various physiologic/pathologic states, but it is not without its drawbacks.

Nevertheless, the studies relating to the potential role of T1ρ-weighted MRI in measuring cartilage degeneration have all been restricted to single slice imaging, and hence, are impractical for the imaging of a typical anatomic volume. The use of single slice techniques results from the problem in making the spin-locking pulse slice selective, whereas multi-slice imaging requires the application of multiple radio frequency (RF) pulse trains within a sequence repetition time (TR) to excite several slices in a time efficient manner. Currently, T1ρ pulse sequences employ a non-selective RF pulse to spin-lock the magnetization in the transverse plane following the application of a non-selective π/2 pulse, exciting signals from the entire sample during each application, but the subsequent imaging sequence acquires data from only a single slice, wasting the information from the remainder of the volume. Additionally, significant artifacts arise in T1ρ-weighted imaging when mutation angles suffer small deviations from their expected values that vary with spin-locking time and amplitude, severely limiting attempts to perform quantitative imaging or measurement of T1ρ relaxation times.

The current lack of adequate methods for quantifying these changes has hampered research directed towards the development of potential disease modifying agents.

SUMMARY OF THE INVENTION

To solve these and other problems, the present invention as described herein, introduces a method of, and system for, magnetic resonance imaging of diagnostic mapping of tissues, where sodium mapping is performed individually, as well as in combination with other images of tissue, such as T1ρ, T2, and/or T1-weighted images.

In one method embodiment, a first image of a tissue is acquired during a scanning session. The first image includes a T1ρ, T2, and/or T1-weighted image of the tissue. A sodium (e.g., Na) image of the tissue is acquired during the same scanning session. Maps are constructed of each of the first and Na images individually, and in combination with each other. This construction facilitates viewing the first and Na images individually or in combination with each other as a single, blended image of the tissue.

The methods and systems of the invention may be adapted for use with a wide array of clinical assessments, such as, but not limited to: intervertebral disk pathology, tumors, to study Alzheimer's disease, neuro-degeneration, myocardial abnormalities, arthritis, joint injuries and abnormalities, heart disease, and scanning cartilage pathology. An integrated, and noninvasive measurement of molecular (PG, collagen and water) and morphological (tissue volume) changes in cartilage by the method and system herein, also enables the detection of OA, in its early stages.

The imaging allows for more effective diagnosis of these conditions, through improved, comprehensive, and noninvasive imaging techniques. These measurements will help monitor disease progression, evaluate potential strategies for disease management, and verify the efficacy of disease/disease modifying drugs.

In one embodiment, the use of the imaging modalities of T1ρ with sodium imaging for diagnostic imaging of pathologies such as Alzheimer's disease, osteoarthritis, intervertebral-disc disease are techniques that may be used in combination or individually along with conventional MRI contrast mechanisms (T1, T2) provides surprising and unexpected results than when performed individually heretofore. Thus, the inventors have discovered the relationship between sodium, T1ρ, and other contrast mechanisms, which provide the ability to more readily view images, and detect and diagnose the diseases process earlier than can be done before this invention.

Reference herein to "one embodiment," "an embodiment" or similar formulations herein, means that a particular feature, structure, operation, or characteristic described in connection with the embodiment, is included in at least one embodiment of the present invention. Thus, the appearances of such phrases or formulations herein are not necessarily all referring to the same embodiment. Furthermore, various particular features, structures, operations, or characteristics may be combined in any suitable manner in one or more embodiments.

Additional objects, advantages and novel features of the invention will be set forth in part in the description, examples and figures which follow, and in part will become apparent to those skilled in the art on examination of the following, or may be learned by practice of the invention.

BRIEF DESCRIPTION OF THE DRAWINGS

The detailed description is explained with reference to the accompanying figures. In the Figures, the left-most digit(s) of the reference number identifies the figure in which the reference first appears.

DETAILED DESCRIPTION OF CERTAIN EMBODIMENTS OF THE INVENTION

Magnetic Resonance Imaging (MRI) is an imaging technique based in part on the absorption and emission of energy in the radio frequency range. To obtain the necessary magnetic resonance (MR) images, a patient (or other target) is placed in a magnetic resonance scanner. The scanner provides a magnetic field that causes target atoms to align with the magnetic field. The scanner also includes coils that apply a transverse magnetic field. Radio-frequency (RF) pulses are emitted by the coils, causing the target atoms to absorb energy. In response to the RF pulses, photons are emitted by the target atoms and detected as signals in receiver coils.

Present diagnostic strategies, such as CT, and T1- and T2-weighted magnetic resonance imaging, are only sensitive in advanced stages of the disease. Described herein is an innovative MR package that provides complete information about the biochemical and morphological state of the tissue. The MR package includes a process of pre-imaging, image-acquisition, post-processing, and image-viewing steps designed for physicians to diagnose tissues at earlier stages of disease.

Figure 1:
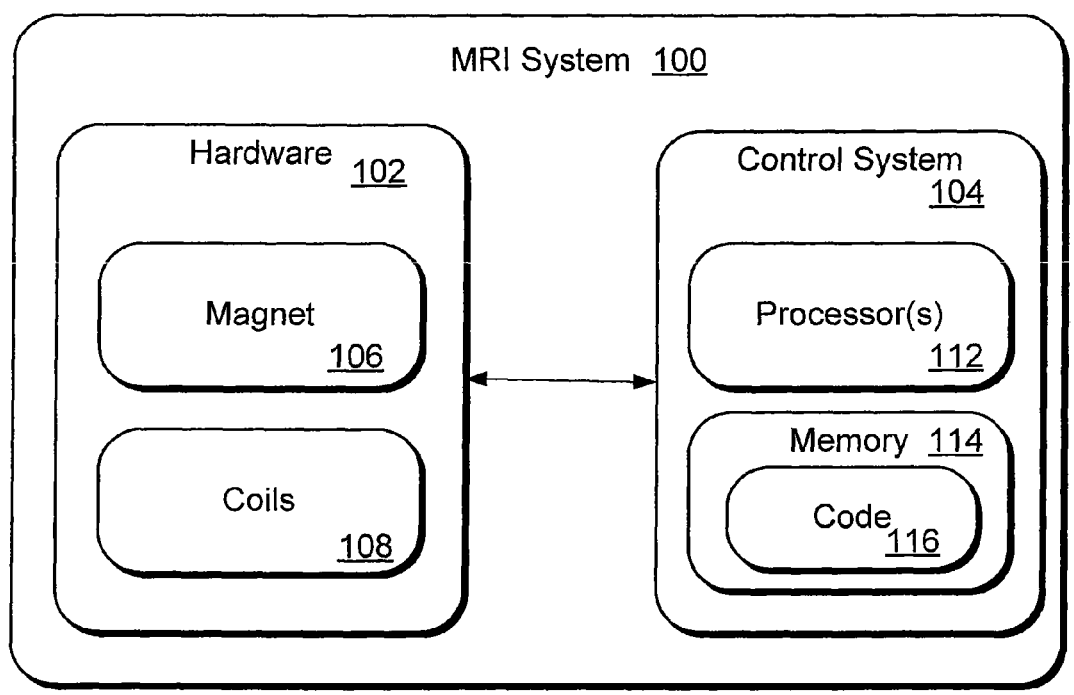
FIG. 1 illustrates an MRI system within which the present invention can be either fully or partially implemented.

FIG. 1 illustrates an MRI system 100 within which the present invention can be either fully or partially implemented. As appreciated by those skilled in the art, there are various ways to implement an MRI system 100. In one possible embodiment, MRI system 100 includes hardware components 102, and a control system 104. As is well known by those skilled in the art, typical hardware components 102 include: a magnet 106 for producing a stable and very intense magnetic field, and may include one or more coils, such as gradient coil for creating a variable field, and radio frequency (RF) coil, for transmitting energy and encoding spatial positioning.

Control system 104 controls hardware components 102, such as the scanning sequencing operations, and processes information obtained from scanning. Control system 104 may be implemented as a computer or control device, which includes at least one processor 112, and memory 114. Memory 114 may include volatile memory (e.g., RAM) and/or non-volatile memory (e.g., ROM). It is also possible for other memory mediums (not shown) having various physical properties to be included as part of control system 104. The images and maps provided using such systems are referred to as "computer-generated."

Control system 104 may also include code 116 stored in memory 114, such as software and/or firmware that causes MRI system 100 to perform scanning, and processing of images.

Much of the discussion below will focus on embodiments for performing operations of control system 104—that may be embodied as code 116 or media—used to control MRI system 100. In particular, image acquisition, post processing, and image viewing stages. As appreciated by those skilled in the art, any suitable pre-imaging techniques may be used prior to acquiring images.

As used herein, the term "acquiring," "acquire," or variations thereof, refers to the act of (i) receiving data signals indicative of images received from hardware 102 and stored as data in memory 114, or (ii) sending instructions to hardware 102 from control system 104 to obtain the images, and then obtaining/storing the images, or (iii) reading data from memory 114 corresponding to images previously received from hardware 102, and stored in memory, (iv) or any combination of thereof.

Figure 2:
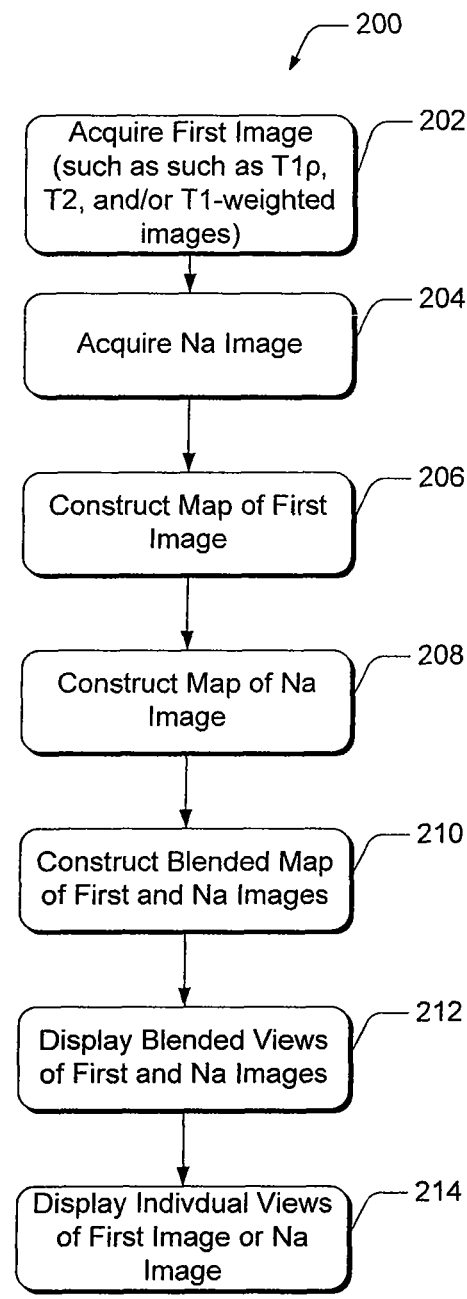
FIG. 2 is an exemplary method for performing imaging acquisition through the use of an MRI system, such as the system of FIG. 1.

FIG. 2 is an exemplary method 200 for performing imaging acquisition through the use of an MRI system, such as system 100 of FIG. 1. Method 200 includes blocks 202, 204, 206, 208, 210, and 212 (each of the blocks represents one or more operational acts). The order in which the method is described is not to be construed as a limitation, and any number of the described method blocks may be combined in any order to implement the method. Furthermore, the method can be implemented in any suitable hardware, software, firmware, or combination thereof. Additionally, although each module in FIG. 2 is shown as a single block, it is understood that when actually implemented in the form of computer-executable instructions, media, logic, firmware, and/or hardware, that the functionality described with reference to it, may not exist as separate identifiable block.

In block 202 of FIG. 2, a first image of a tissue during a scanning session is acquired. The first image may include T1ρ, T1-weighted, and/or T2 images of a localized tissue (in general, collectively referred to as a T-image for claim purposes). The acquisition of the first image may involve several subcategories of operations.

For example, in one embodiment, MRI system 100 (FIG. 1) may acquire a three-plane image of localized tissue. It is presumed that pre-imaging techniques are performed prior to, or concurrent with, acquisition of a three-plane image.

If the tissue has previously been imaged, MRI system slice planning can be coordinated by real-time coregistration of old and new localizers.

Another subcategory step of block 202 may include acquiring a three-dimensional T1-weighted isotropic resolution scan with full coverage of the tissue. Alternatively, in other embodiments, T2 image scans with full cover the tissue may be acquired.

In one embodiment, as another potential subcategory operation of block 202, multiple T1ρ-weighted images with incremental spin lock duration and/or amplitude are also acquired, covering the same volume as T1-weighted images.

In block 204, an Na image of the tissue is acquired during the same scanning session as the acquisition of the first image in block 202. This operational block may also involve several subcategories operations.

For example, in one embodiment, if a spectrometer (not shown) of MRI system 100 (FIG. 1) has multiple RF channels capable of broadband or dual-band RF transmission and signal reception, then concurrent with both T1- and T1ρ-weighted image acquisition in block 202, an ultrashort TE or radial magic echo of $^{23}$Na images may be acquired. As appreciated by those skilled in the art having the benefit of this disclosure, in alternative embodiments, other quantities of Na images may be acquired.

Alternatively, in another embodiment, if the spectrometer of MRI system 100 (FIG. 1), does not have multiple RF channels, but is capable of broadband RF transmission and signal reception, then ultra short TE radial or radial magic echo $^{23}$Na images are acquired during the $^{1}$H magnetization regrowth period between balanced Steady-State Free Precession (bSSFP) readout and the next spin-lock duration. This time is equivalent to TR-SL-bSSFP-PREP, where SL denotes the spin lock duration, bSSFP denotes the readout duration and PREP denotes the duration of any additional preparation periods, i.e. dummy pulses (linear, constant or otherwise), fat saturation periods or inversion recovery periods. TR is the delay between subsequent acquisitions.

In one embodiment, pre-preparation involves several optional RF and gradient pulses that may be activated at any time during a sequence to modify T1ρ contrast. It is appreciated by those skilled in the art after having the benefit of this disclosure that preparation periods may be used to complement T1ρ imaging in order to reduce blurring, artifacts, etc. These are not necessarily mutually exclusive from the image acquisition period. Examples of pre-preparation pulses include, but are not limited to, Inversion, Gradient Tagging, Diffusion-Weighting, and Spectral Excitation/Saturation.

In one embodiment, any of the foregoing operations may be repeated using a coronal view. As appreciated by those skilled in the art, having the benefit of this disclosure may be included as part of process 200. Alternatively, obtaining images from the perspective of the coronal view may not be performed.

While FIG. 2 shows a specific example of image acquisition process, it should be understood by those skilled in the art, after having the benefit of this disclosure that acquisition of a first image (such as T1ρ, T2, and/or T1-weighted image) may be performed in combination with the acquisition of the Na image. The exact techniques used to acquire these images may vary. Thus, many modifications to the sequence of operations shown in FIG. 2 may achieve the same result of image acquisition. Some examples of generalizations of the pulse sequence include interleaved sodium and proton MRI, or alternately proton and sodium images.

Figure 3:
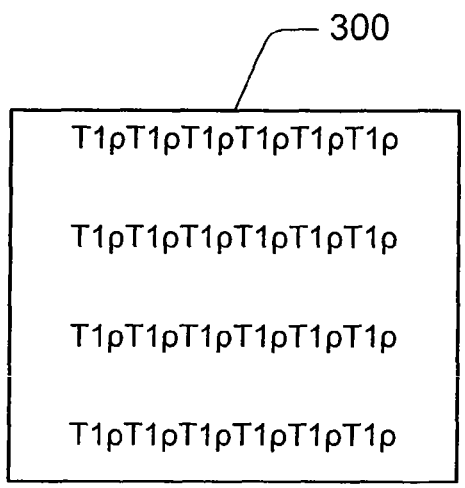
FIG. 3 shows a pseudo map of a T1ρ image of a tissue.

In block 206, a map of the first image (first T-image) is constructed. For example, T1ρ images are constructed from multiple T1ρ-weighted and stored in memory 114 (FIG. 1). Such maps are computer-generated from the acquired images entered into the computer. FIG. 3 shows a map 300 of a T1ρ image of a tissue.

Referring back to FIG. 2, T1-weighted images are constructed. T2 images may also be constructed. Maps may also be semi-automatically segmented for viewing, presentation or display. T1ρ-weighted images or T2 images, are combined using any suitable volumetric or multiple slice imaging sequence on a computer, as would be appreciated by those skilled in the art.

Figure 4:
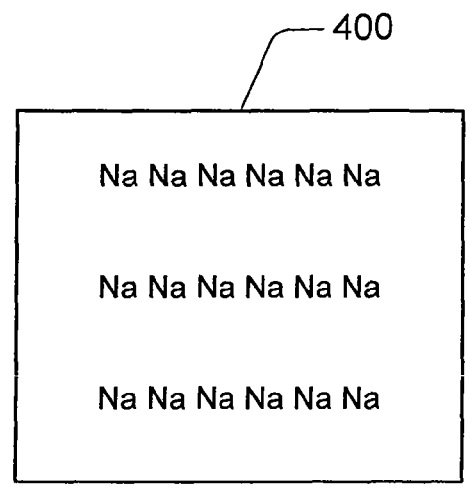
FIG. 4 shows a pseudo map of a Na image of a tissue.

In block 208, a map of the Na image is constructed and stored in memory 114 (FIG. 1). Sodium concentration (FCD) maps are constructed from normalized phantoms contained within the imaging region of interest or field of view (FOV). FIG. 4 show a pseudo map 400 of a Na image of a tissue.

Referring back to FIG. 2, in block 210, a blended mapping of the first and Na images is constructed and stored in memory 114 (FIG. 1). For example, in one embodiment, T1ρ images are co-registered with T1-weighted, and sodium images to correct for motion that occurred during the scan if any did occur. If there were no motion, there would be no motion correction, but they may still be blended together. T1-weighted images (volume data) are combined with the T1ρ relaxation times (ti) and Na concentration to provide at least two metrics for tissue assessment.

Figure 5:
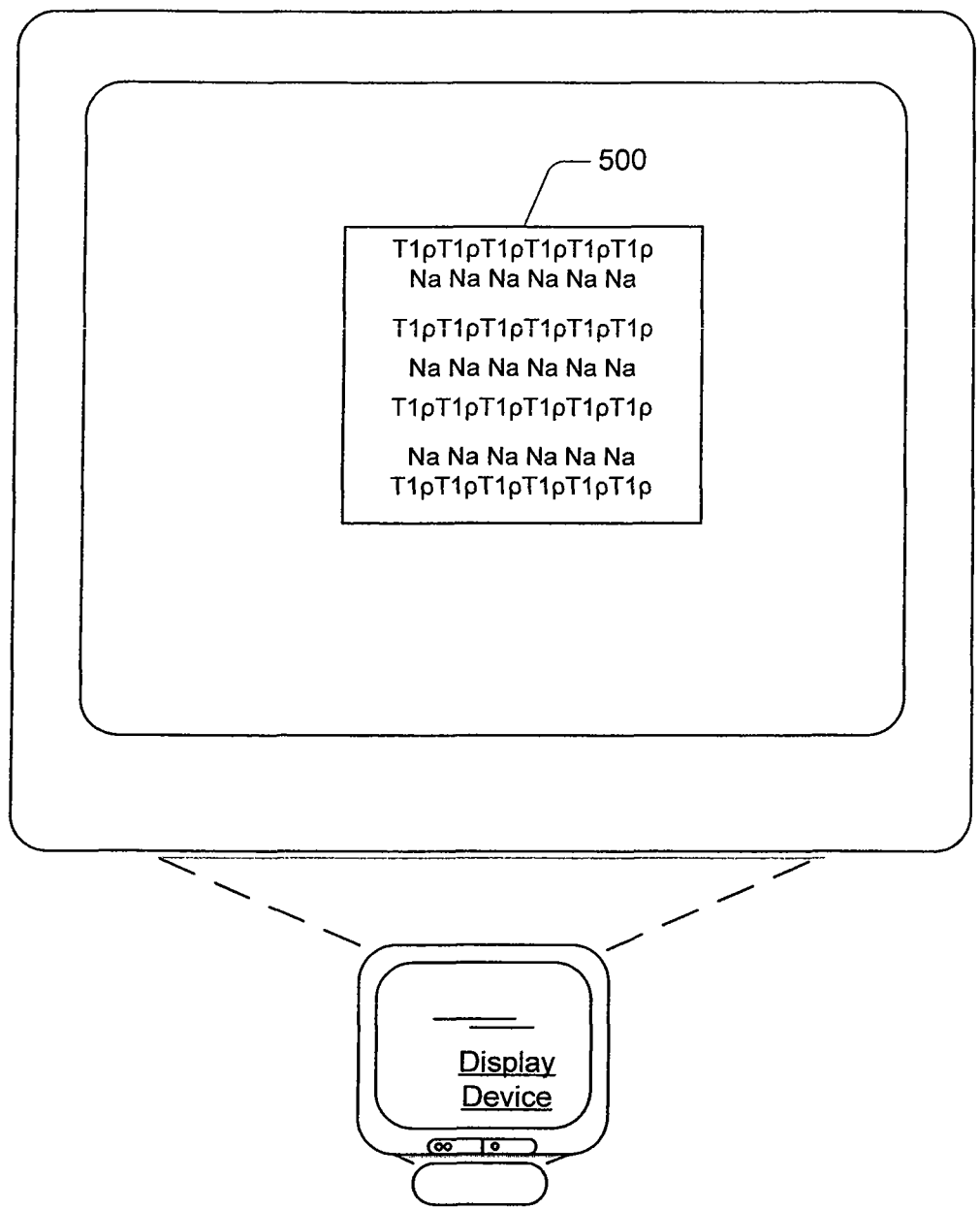
FIG. 5 shows a pseudo-blended view of T1ρ images (that may or may not include T1 and/or T2 with images) blended with Na images.

In block 212, a blended view of maps 300 and 400 are viewable and/or displayed, as a blended view 500 (FIG. 5) of the tissue. That is, multi-parameter image maps (such as shown in FIGS. 3 and 4) are uploaded to an image viewing database displayed. A user may then select to display a blended view 500 of the T1 and or T2 with T1ρ and or Na images, such as shown in FIG. 5. Or alternatively, the user may select to view the maps individually, per block 214 of FIG. 2. That is, the user may select to display a single modality image and query the parameter values of the other two images by cursor inspection, or region-of-interest (ROI) analysis.

As a result of using method 200, a comprehensive tissue-mapping package may now be made available to physicians for diagnosing osteoarthritis, breast cancer, intervertebral-disk pathology, tumors, Alzheimer's disease, and neuro degeneration, among others. With respect to osteoarthritis, method 200 allows for T1ρ relaxation mapping, sodium mapping, and T2 mapping of the joints for OA diagnosis, particularly in the early stages.

In alternative embodiments, a magnetic-resonance-imaging system is provided, the system having pulses delivered by RF scanner coil(s), wherein the system comprises: a device in the system for acquiring onto a computer, a T1ρ image of a tissue during a scanning session; a device in the system for acquiring onto the computer, an Na image of the tissue during the same scanning session; a computer means for constructing computer-generated maps of each of the T1ρ image and the Na images individually, and simultaneously in combination with each other, such that the T1ρ and Na images are viewable in at least one of individually and in combination with each other as a single, blended image of the tissue; and a device for displaying same. Also provided is an MRI system further comprising: a device for acquiring a T1-weighted image during the same scanning session, and constructing a computer-generated map of the T1-weighted image in combination with the T1ρ and Na images, such that the T1-weighted, T1ρ, and Na images are viewable as a single, blended image of the tissue; and a device for displaying the T1-weighted, T1ρ, and Na images as a single, blended image of the tissue. In addition, an MRI system is provided, further comprising: a device for acquiring a T2 image during the same scanning session, and constructing a map of the T2 image in combination with the T1ρ, T1-weighted, and Na images, such that the T2, T1ρ, T1-weighted and Na images are viewable as a single, blended image of the tissue; and a device for displaying the T2, T1ρ, T1-weighted and Na images as a single, blended image of the tissue.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. The embodiments described herein are to be considered in all respects only as exemplary and not restrictive. The scope of the invention is, therefore, indicated by the subjoined claims rather by the foregoing description. All changes which come within the meaning and range of equivalency of the claims are to be embraced within their scope.

What is claimed is:

1. A method for magnetic resonance imaging (MRI) for diagnostic mapping of tissue, the MRI system having pulses delivered by RF scanner coil(s), the method comprising:
   acquiring a first T-image of the tissue during a scanning session, wherein the first image includes at least one of a T1ρ, a T1-weighted, and a T2 image;
   acquiring a Na image of the tissue during the same scanning session; and
   constructing computer-generated maps of each of the first T-image and Na image individually, and in combination with each other, such that the first and Na images are viewable in at least one of individually and in combination with each other as a single, blended image of the tissue.

2. The method of claim 1, further comprising simultaneously displaying the first T-image and the Na image in combination with each other, as a single, blended image of the imaged tissue.

3. The method of claim 2, further comprising studying cartilage pathology and arthritis utilizing the simultaneously displayed first T-image and Na image in combination with each other.

4. The method of claim 2, further comprising studying any of the following:
   intervertebral disk pathology, tumors, Alzheimer's disease, or neurodegeneration, utilizing the simultaneously displayed first T-image and Na image in combination with each other.

5. The method of claim 1, wherein the first T-image and the Na image are three-plane images of the tissue.

6. The method of claim 1, wherein the first T-image is a T1ρ image.

7. The method of claim 6, further comprising studying any of the following: cartilage pathology and arthritis, intervertebral disk pathology, tumors, Alzheimer's disease, or neurodegeneration utilizing the simultaneously displayed first T-image and Na image in combination with each other.

8. One or more computer-readable media for magnetic resonance imaging for diagnostic mapping of tissue, the medium having computer-executable instructions, which when executed by one or more processors of the MRI system having pulses delivered by RF scanner coil(s), cause the device to perform the steps of claim 1.

9. A method for magnetic resonance imaging (MRI) for diagnostic mapping of tissue, the MRI system having pulses delivered by RF scanner coil(s), the method comprising:
   acquiring a T1ρ image of the tissue during a scanning session;
   acquiring a Na image of the tissue during the same scanning session;
   constructing a computer-generated map of each of the T1ρ image and the Na image individually, such that the T1ρ image and the Na images are viewable individually;
   constructing a computer-generated map of each of the T1ρ image and the Na image in simultaneous combination, such that the T1ρ and Na images are viewable as a single, blended image of the tissue; and
   displaying the single, blended image of the tissue.

10. The method of claim 9, further comprising using the single, blended image of the tissue to study cartilage pathology and arthritis.

11. The method of claim 9, further comprising using the single, blended image of the tissue to study at least one of: intervertebral disk pathology, tumors, Alzheimer's disease, and neuro degeneration.

12. The method of claim 9, furthering comprising: acquiring a T1-weighted image during the same scanning session, and constructing a computer-generated map of the T1-weighted image in combination with the T1ρ and Na images, such that the T1-weighted, T1ρ, and Na images are viewable as a single, blended image of the tissue; and displaying the T1-weighted, T1ρ, and Na images as a single, blended image of the tissue.

13. The method of claim 12, further comprising using the single, blended image of the tissue to study cartilage pathology and arthritis.

14. The method of claim 12, further comprising using the single, blended image of the tissue to study at least one of: intervertebral disk pathology, tumors, Alzheimer's disease, and neuro degeneration.

15. The method of claim 12, further comprising: acquiring a T2 image during the same scanning session, and constructing a map of the T2 image in combination with the T1ρ and Na images, such that the T2, T1ρ, and Na images are viewable as a single, blended image of the tissue; and displaying the T2, T1-weighted, T1ρ, and Na images as a single, blended image of the tissue.

16. The method of claim 15, further comprising using the single, blended image of the tissue to study cartilage pathology and arthritis.

17. The method of claim 15, further comprising using the single, blended image of the tissue to study at least one of: intervertebral disk pathology, tumors, Alzheimer's disease, and neuro degeneration.

18. A magnetic-resonance-imaging system, having pulses delivered by RF scanner coil(s), the system comprising:
   device in the system for acquiring onto a computer, a T1ρ image of a tissue during a scanning session;
   device in the system for acquiring onto the computer, an Na image of the tissue during the same scanning session;
   computer means for constructing computer-generated maps of each of the T1ρ image and the Na images individually, and simultaneously in combination with each other, such that the T1ρ and Na images are viewable in at least one of individually and in combination with each other as a single, blended image of the tissue; and
   device for displaying same.

19. The system of claim 18, furthering comprising: device for acquiring a T1-weighted image during the same scanning session, and constructing a computer-generated map of the T1-weighted image in combination with the T1ρ and Na images, such that the T1-weighted, T1ρ, and Na images are viewable as a single, blended image of the tissue; and device for displaying the T1-weighted, T1ρ, and Na images as a single, blended image of the tissue.

20. The system of claim 19, further comprising: device for acquiring a T2 image during the same scanning session, and constructing a map of the T2 image in combination with the T1ρ, T1-weighted, and Na images, such that the T2, T1ρ, T1-weighted and Na images are viewable as a single, blended image of the tissue; and device for displaying the T2, T1ρ, T1-weighted and Na images as a single, blended image of the tissue.

* * * * *